US006491655B1

United States Patent
Pollard et al.

(10) Patent No.: US 6,491,655 B1
(45) Date of Patent: Dec. 10, 2002

(54) METHODS FOR TREATING HEMOPHILIA A AND B AND AIDS AND DEVICES USED THEREIN

(76) Inventors: Harvey B. Pollard, 11008 Lamplighter La., Potomac, MD (US) 20854; Bette S. Pollard, 1008 Lamplighter La., Potomac, MD (US) 20854

( * ) Notice: Subject to any disclaimer, the term of this patent is extended or adjusted under 35 U.S.C. 154(b) by 0 days.

(21) Appl. No.: 09/516,769

(22) Filed: Mar. 1, 2000

Related U.S. Application Data

(63) Continuation-in-part of application No. 09/205,964, filed on Dec. 4, 1998, which is a division of application No. 08/772,034, filed on Sep. 26, 1996, now Pat. No. 5,908,399, which is a continuation of application No. 08/050,370, filed on Dec. 21, 1993, now abandoned, which is a continuation-in-part of application No. 07/941,573, filed as application No. PCT/US92/07627 on Sep. 9, 1992, now abandoned, which is a continuation-in-part of application No. 07/756,621, filed on Sep. 9, 1991, now abandoned.

(51) Int. Cl.$^7$ .............................................. A61M 37/00
(52) U.S. Cl. .................. 604/5.02; 604/93.01; 210/679; 424/424
(58) Field of Search .............................. 210/679, 502.1; 604/401, 5.02, 500, 502, 514, 522, 93, 57; 424/422, 424, 491, 423; 436/289, 297.1

(56) References Cited

U.S. PATENT DOCUMENTS 4,409,105 A * 10/1983 Hayashi et al.
4,863,611 A * 9/1989 Bernstein et al.
4,923,457 A * 5/1990 Ellingsen
4,960,415 A * 10/1990 Reinmuller
5,026,365 A * 6/1991 Rossini et al.
5,387,237 A * 2/1995 Fournier et al.
5,487,739 A * 1/1996 Aebischer et al.
5,554,148 A * 9/1996 Aebischer et al.
5,855,616 A * 1/1999 Fournier et al.

* cited by examiner

Primary Examiner—Mark Bockelman
(74) Attorney, Agent, or Firm—Dennis H. Lambert

(57) ABSTRACT

The present invention provides a method for treating Hemophilia A or B which comprises implanting in fluid communication with the bloodstream of a mammal in need of such treatment a permeable membrane having one or more walls, a hollow chamber therewithin, a plurality of holes extending through the walls of the membrane and permitting fluid to enter and exit the chamber of the membrane, each of the holes being sized so that it is large enough to permit inactive Factor VII to enter the chamber of the membrane and activated Factor VIIa to exit the chamber of the membrane but small enough to prevent fibrinogen from entering the chamber of the membrane, a plurality of supports being disposed within the chamber, and an effective amount of a Factor VII activator or a source of the activator being bound to the supports, wherein inactive factor VII in blood passing through the membrane becomes activated into Factor VIIa upon contact with the activator within the chamber.

The present invention also provides a method for treating Hemophilia A or B extracorporeally. The present invention further provides methods for treating AIDS as well as permeable membranes for use in the methods above.

10 Claims, 9 Drawing Sheets

METHODS FOR TREATING HEMOPHILIA A AND B AND AIDS AND DEVICES USED THEREIN

RELATED APPLICATIONS

This application is a continuation-in-part of Ser. No. 09/205,964, filed Dec. 4, 1998, which is a divisional of Ser. No. 08/772,034, filed Sep. 26, 1996, now U.S. Pat. No. 5,908,399; which is a continuation of Ser. No. 08/050,370, filed Dec. 21, 1993, abandoned; which is a continuation-in-part of Ser. No. 07/941,573, filed Sep. 9, 1992, abandoned, and a 371 of PCT/US92/07627, filed Sep. 9, 1992, abandoned, which is a continuation-in-part of Ser. No. 07/756,621, filed Sep. 9, 1991, abandoned.

GOVERNMENT LICENSE RIGHTS

Purusant to 15 USC §3710(d) and 37 CFR §501.6(a)(2), the United States Government retains a non-exclusive, irrevocable, royalty-free license in the invention with authority to grant licenses for all government purposes.

BACKGROUND OF THE INVENTION

Hemophilia A and B are due to a deficiency of Factor VIII and IX, respectively. These factors are required in concert to activate Factor X to Factor Xa by the intrinsic pathway,

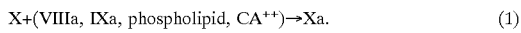

$$X+(VIIIa, IXa, phospholipid, CA^{++}) \rightarrow Xa. \quad (1)$$

The treatment of choice for these disorders is presently replacement therapy, and is the basis of a one billion dollar per year business worldwide.

Very recently, recombinant Factor VIIa (NOVO, Denmark) has been shown to have therapeutic value for Hemophilia A and B in dogs (Brinkhaus, K M et al. (1989) *Proc. Nat. Acad. Sci.* (*USA*) 86:1382–1386), and trials with humans have been initiated (Hadner, U. et al. (1988) *Lancet II,* 1193; Macik, R G et al. (1988) *Blood* 72:320a (Abstract 1117)). The mechanism by which Factor VIIa is therapeutic seems to be by direct activation of Factor X to Xa, which then feeds back and activates additional Factor VII to VIIa (Rao, L V M and Rapaport, E I (1990) *Blood* 5:1069–1073). Both the recombinant (r-) Factor VIIa and the newly generated VIIa then bind to exposed Tissue Factor, and together this complex activates X to Xa by the extrinsic pathway,

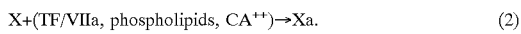

$$X+(TF/VIIa, phospholipids, CA^{++}) \rightarrow Xa. \quad (2)$$

The extrinsic pathway in hemophilia patients is normal, but since all of Factor VII is in the inactivated state, little or no activation of the extrinisc pathway occurs when needed. Apparently, the intrinsic pathway is needed for tonic activation of Xa and generation of VIIa. The relative rate of conversion of X to Xa by VIIa alone is 15 million-fold less than the rate observed when VIIa is complexed with Tissue Factor (Bom, V J J and Bertina, R M (1990) *Biochem. J.* 265:327–336). Nonetheless, the small amount of Xa generated by the administration of r-Factor VIIa is sufficient to reduce bleeding in afflicted patients.

A critical problem yet to be solved is the fact that r-Factor VIIa itself has a short half-life (about 2 hours). This means that sustained, exogenous replacement of this material would be necessary for treating patients. The present invention avoids the need for exogenous replacement (e.g. hourly or daily therapy in the case of accident, or preventive therapy in the event of dental or surgical procedures (Hadner, U. et al. (1988) *Lancet II,* 1193)) by employing the patient's own Factor VII to generate activated Factor VII (Factor VIIa).

Treatment of human immunodeficiency virus (HIV-1) infection, and of the acquired immunodeficiency syndrome (AIDS), has been developing slowly since the burst of activity culminating in 1988 (see Gallo and Montagnier *Scientific American* 259 (4): 41–48 (1988): Weber and Weiss *Scientific American* 259 (4): 101–109) (1988).

The principle targets of the HIV virions are the T-4 type T lymphocytes. The virus attaches itself through interaction between envelope gp120 molecules (McKeating, J. A. and R. A. Wiley *AIDS* 3 (*Suppl.* 1) S35-41 (1989); Kieber-Emmons, et al. *Biochem.Biophys.Acta.* 989:281–300 (1991); Gelderblom, H. R. *AIDS* 5:617–638 (1991); and Capon, D. J. and R. H. R. Ward *Ann.Rev.Immunl.* 9:646–678) (1991)), and the CD4 receptor molecules on the cell surface (Sweet, R. W., et al. *Curr. Opin. in Biotechnol.* 2:622–633 (1991); Grewe, C., et al. *J. Acquired Immun. Def. Syndrome* 3:965–974 (1990)). The bound virus then enters the cell by fusing with the cell membrane (Dalgleish, A. G., et al. *Nature* 312:763–767 (1984); Sattenau, Q. J. and Weiss, R. A. *Cell* 52:631–632 (1984); Robey E. and R. Axel *Cell* 60:697–700 (1990)). HIV also can enter and reside in macrophages and some neurons, since these cells also express the CD4 receptor on the cell surface (Madden, P. J., et al. *Cell* 47:333–348 (1986) and Cheng-Mayer, C. *AIDS* 4 (*Suppl.* 1) 549–556 (1990)). AIDS-associated subcortical dementia may begin by the latter mechanism. The CD4 receptor also resides on enterochromaffin cells in the gastrointestinal tract, and may be the reason for the persistent diarrhea which affects 80% of AIDS patients (see descriptions in the American College of Gastroenterology Meeting Highlights, 1990, p. 1 and 6).

Since the CD4 receptor provides the mechanism for specific HIV infection, an attractive strategy has involved possible administration of free r-CD4 receptor or specific subdomains of the receptor (Arthos, J., et al. *Cell* 57:469–481 (1989) and Sweet, R. W., et al. *Curr. Opin. in Biotechnol.* 2:622–633 (1991)) to AIDS patients. According to this concept, the freely diffusing CD4 molecules would bind to gp120 sites on the virion surface, and thus save cells with resident CD4 receptors from certain infection. The soluble, secreted form of CD4 also has been shown to block HIV-1 infectivity in vitro (Smith, et al. *Science* 238: 1704–1707 (1987)). Recombinant CD4 (rCD4) also has been prepared by a number of pharmaceutical houses and Universities, including Genetech, Biogen NV, Columbia University, Smith-Kline-Beachum, the Dana-Farber Cancer Center, and the Basel Institute for Immunology (Yarchoan, et al. *Scientific American* 259: 110–119 (1988)). However, the large doses of rCD4 necessary to sustain continuous administration rapidly outrun available material. In addition, and perhaps more importantly, since free CD4 molecules bind to Class II and major histocompatibility (MHC) antigens on cells (Fleury S., et al. *Cell* 66:1037–1049 (1991)), its use further compromises the immune system beyond that caused by HIV alone (Weber, J. N. and Weiss, R. A. *Scientific American* 259:101–109 (1988)).

The present invention avoids the problems associated with continuous administration of free rCD4 by keeping the CD4 molecules in contact with body fluids but out of contact with cells which bind to the CD4 molecules.

Buonocore, L. and Rose, J. K. described the production of soluble CD4. The CD4 was mutated with a signal which caused the protein to be retained in the lower endoplasmic veticulum (ER) (Buonocore, L. and Rose, J. K., *Nature,* 345, 625 (1990)). This was found desirable because gp160, the HIV envelope protein precursor, and CD4 bind efficiently in the ER. Buonocore and Rose hypothesized that if CD4 was permanently retained in the ER, it might again block the transport of gp160 to the cell surface. They also hypothesized that a gene expressing the mutated CD4 could be used as gene therapy on AIDS patients. Buonocore and Rose, however, did not teach or suggest a practical method or apparatus by which to utilize CD4.

U.S. Pat. No. 5,109,123, issued Apr. 28, 1992 to Reinherz, et al., described modified human CD4 fragments and their use for diagnostic, therapeutic and preventive purposes. For treatment, Reinherz, et al. disclosed the administration of free modified human CD4 fragments. For preventive purposes, Reinherz, et al. described attaching the CD4 fragments to condoms, spermicides, surgical gloves, and containers or other material for receiving, processing, or storing blood.

Sullivan, et al. described the implementation of artificial pancreas in dogs for administering insulin. (Sullivan et al. *Science,* 252, 718 (1991)). The artificial pancrea incorporated pancreatic islet tissue from healthy dogs and an acrylic housing with a permeable membrane within. The Sullivan, et al. device was connected to the vascular system by graft allowing blood to flow continuously through the device and across the tubular membrane where insulin was released.

SUMMARY OF THE INVENTION

The present invention provides a method for treating Hemophilia A or B which comprises implanting in fluid communication with the bloodstream of a mammal in need of such treatment a permeable membrane which forms one or more walls of a hollow chamber, a plurality of holes extending through the walls and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, wherein inactive Factor VII in blood passing through the membrane becomes activated into Factor VIIa upon contact with the activator within the chamber.

The present invention also provides a method for treating Hemophilia A or B which comprises circulating extracorporeally blood from a mammal in need of such treatment through a permeable membrane which forms one or more walls of a hollow chamber, a plurality of holes extending through the walls and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, wherein inactive Factor VII in blood passing through the membrane becomes activated into Factor VIIa upon contact with the activator within the chamber.

The present invention further provides a permeable membrane forming one or more walls of a hollow chamber, and a plurality of holes extending through the walls and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, the Factor VII activator activating inactive Factor VII in blood passing through the membrane into Factor VIIa upon contact with the inactive Factor VII within the chamber.

In addition, the present invention provides a method for preventing AIDS which comprises implanting in a patient with human immunodeficiency virus a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

The present invention also provides a method for preventing AIDS which comprises administering orally to a patient with human immunodeficiency virus a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

The present invention further provides a method for preventing AIDS which comprises circulating extracorporeally blood from a patient with human immunodeficiency virus through a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

Lastly, the present invention provides a permeable membrane forming one or more walls of a hollow chamber, and a plurality of holes extending through the membrane and permitting fluid to enter and exit the chamber, each of the holes being sized so that it is large enough to permit virions associated with a virus to enter the chamber but small enough to prevent substances capable of binding to virions from entering or exiting the chamber, a plurality of supports being disposed within the chamber, and an effective amount of a substance being bound to the supports, the substance capable of binding to the virions when placed in contact therewith within the chamber thereby preventing such virions from exiting the chamber.

Further objects and advantages of the present invention will be clear from the description as follows.

The Teflon structure was filled with phosphate buffered saline on one side (sol.1) and purified human Factor VII on the other side (Sol.2).

Diffusion of Factor VII through acetate membrane was measured by estimating clotting time. C=at beginning of incubation; Exp.=Experimental after 1 hr. incubation at room temperature. Solid bars represent clotting time of PBS, and striped bars represent clotting time of Factor-VII-containing solution.

Figure 4:
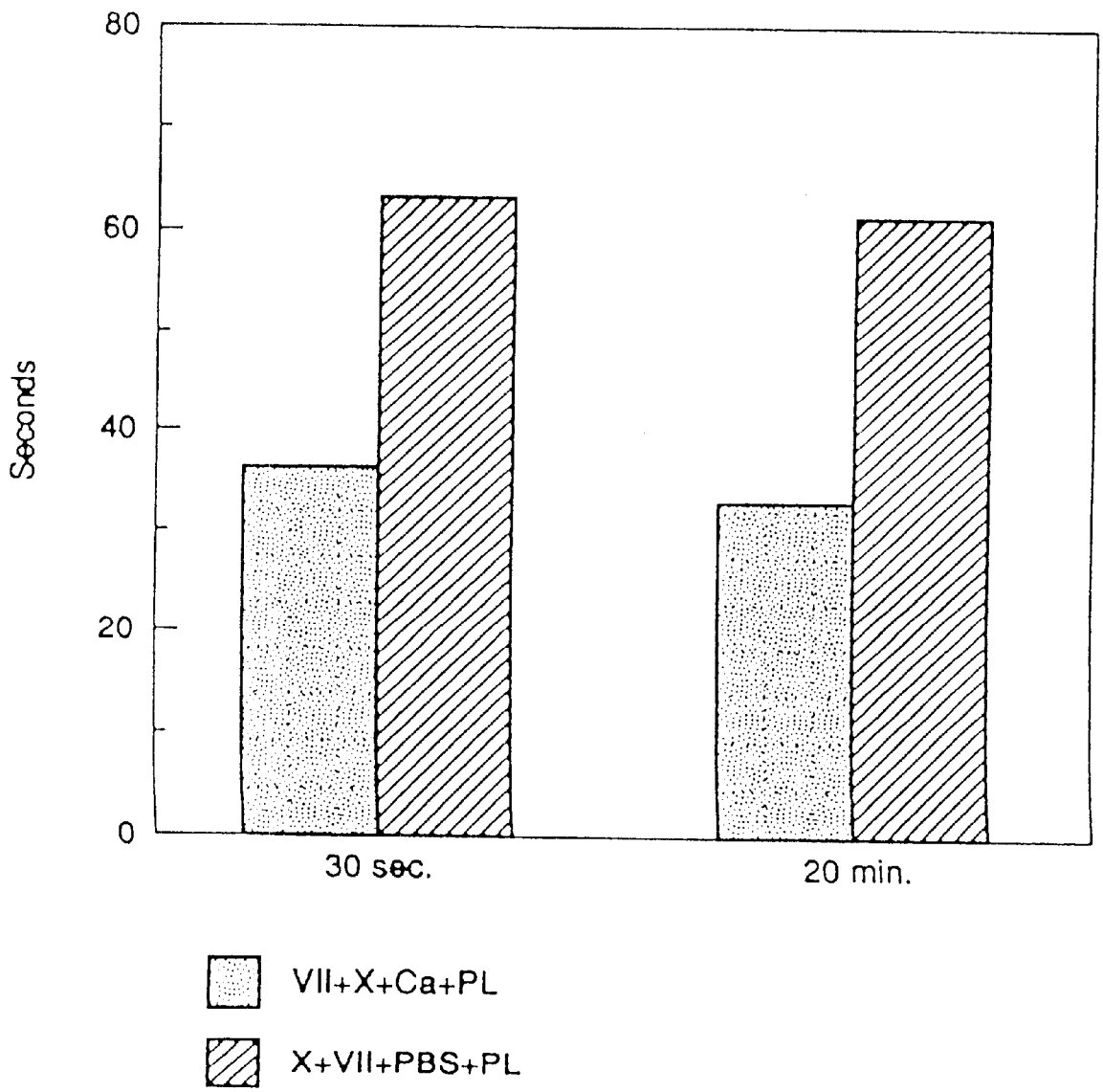

FIG. 4. Activation of purified human Factor VII to VIIa by Factor Xa in the presence or absence of calcium. Factor VII was incubated with Factor Xa and phospholipids in the presence (solid bars) or absence (crosshatched bars) of calcium for 30 sec or 20 min, and PTT activity was measured in seconds (Y-axis).

Figure 5:
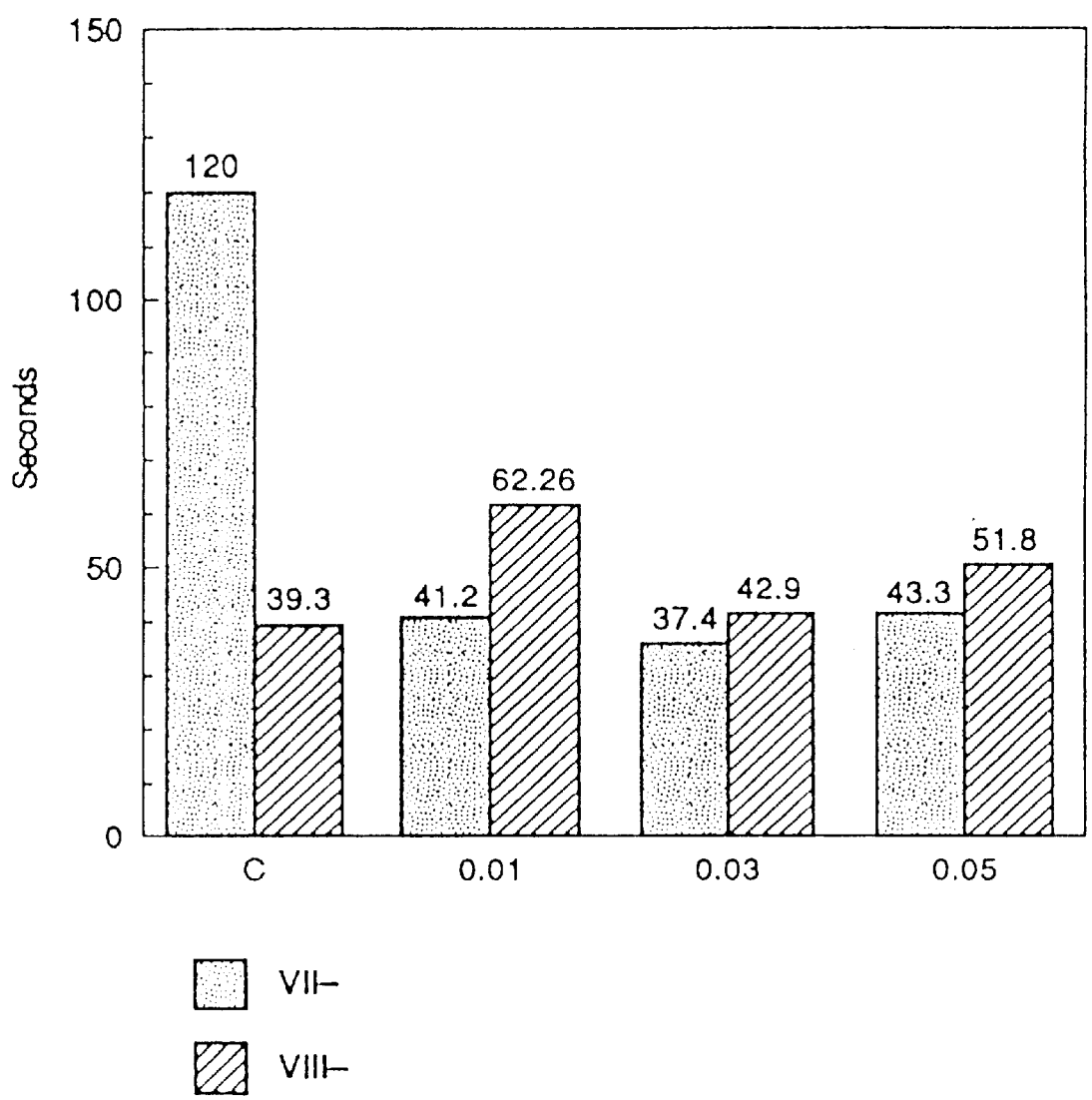

FIG. 5. Ability of Factor VII in plasma to diffuse across a Poretics Polycarbonate Track Etch membrane (PCTE) of defined pore size. A teflon structure with internal volume of 1.0 $cm^3$ was separated from a second test solution by PCTE membrane. Membranes of pore size of 0.01, 0.03, and 0.05 $\mu$m were compared. The two solutions were plasma deficient in Factor VII (solid bars) and plasma deficient in Factor VIII (crosshatched bars). Factor VII was measured in both chambers after incubation for 6 hours at 37° C. using the prothrombin time clotting assay. "C" represents initial clotting time of the Factor VII and Factor VIII deficient plasma.

Figure 6:
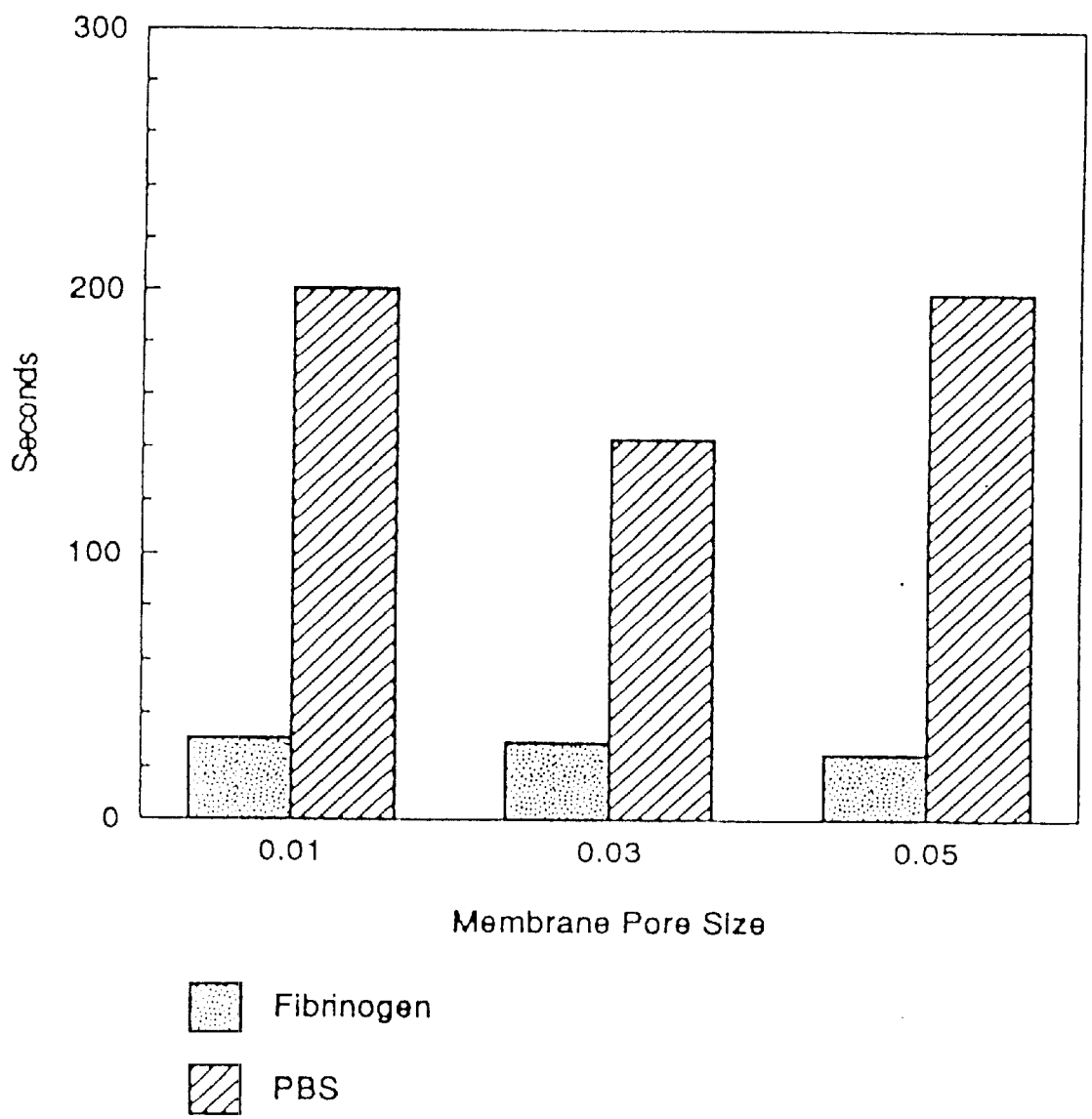

FIG. 6. Ability of Fibrinogen in PBS to diffuse across a Poretics Polycarbonate Track Etch (PCTE) membrane of defined size. A teflon structure with internal volume of 1.0 $cm^3$ was separated from a second test solution by a PCTE membrane. Membranes of pore size 0.01, 0.03 and 0.05 $\mu$m were compared. Two solutions were examined: PBS alone (crosshatched bars) and PBS containing purified human fibrinogen (solid bars) at a concentration and activity equal to that found in human plasma. Fibrinogen was assayed by a conventional method in which activity was estimated from the time thrombin (5 units/ml) could proteolyze the fibrinogen to fibrin and form a clot. Samples of 200 $\mu$l of the 1 ml test solutions were used for the assay.

Figure 7A:
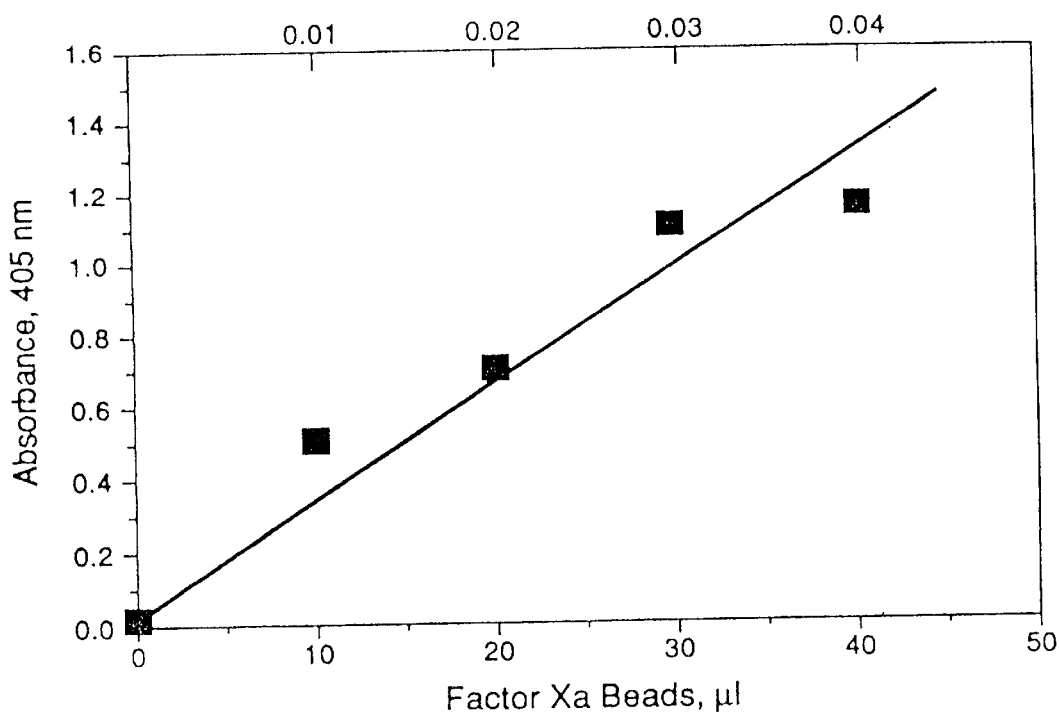

FIG. 7(A). Ability of Factor Xa to form a covalent linkage with beads and retain catalytic activity. Vertical axis represents absorbance of the chromic product of 5-2222 hydrolysis, a specific measure of Factor Xa activity. The upper horizontal axis represents the fraction of the total bead preparation added. The lower horizontal axis is the volume of beads added to the COATEST assay.

Figure 7B:
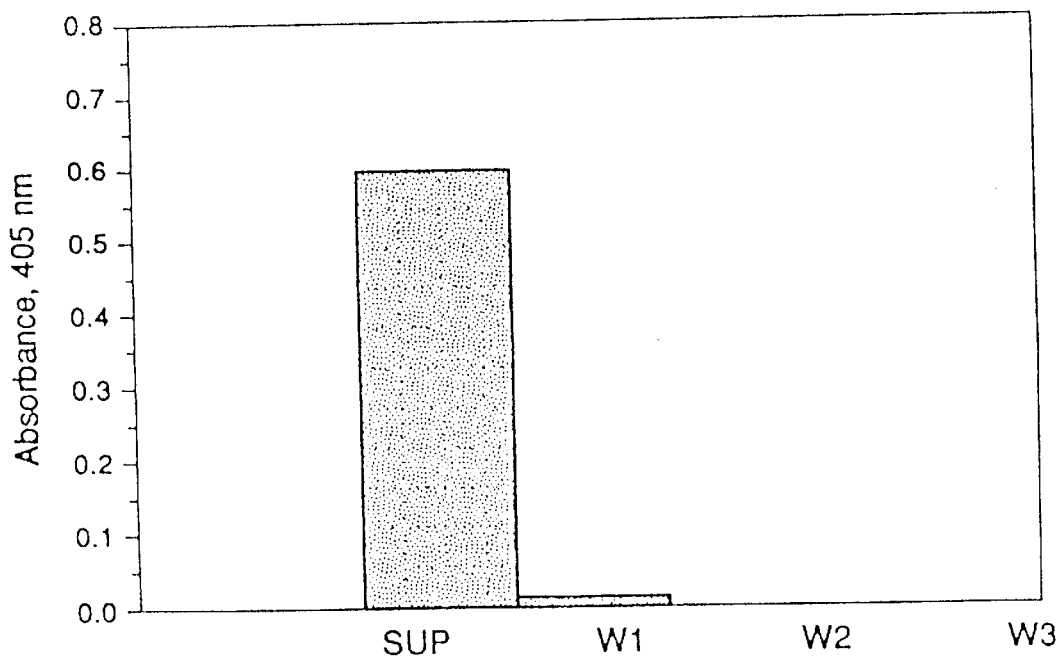

FIG. 7(B). Unbound Factor Xa activity found in 40 $\mu$l of the supernatant solution from the coupling reaction (SUP) W1, W2, and W3 represent unbound Factor Xa activity in 40 $\mu$l aliquots of washing stops.

Figure 8A:
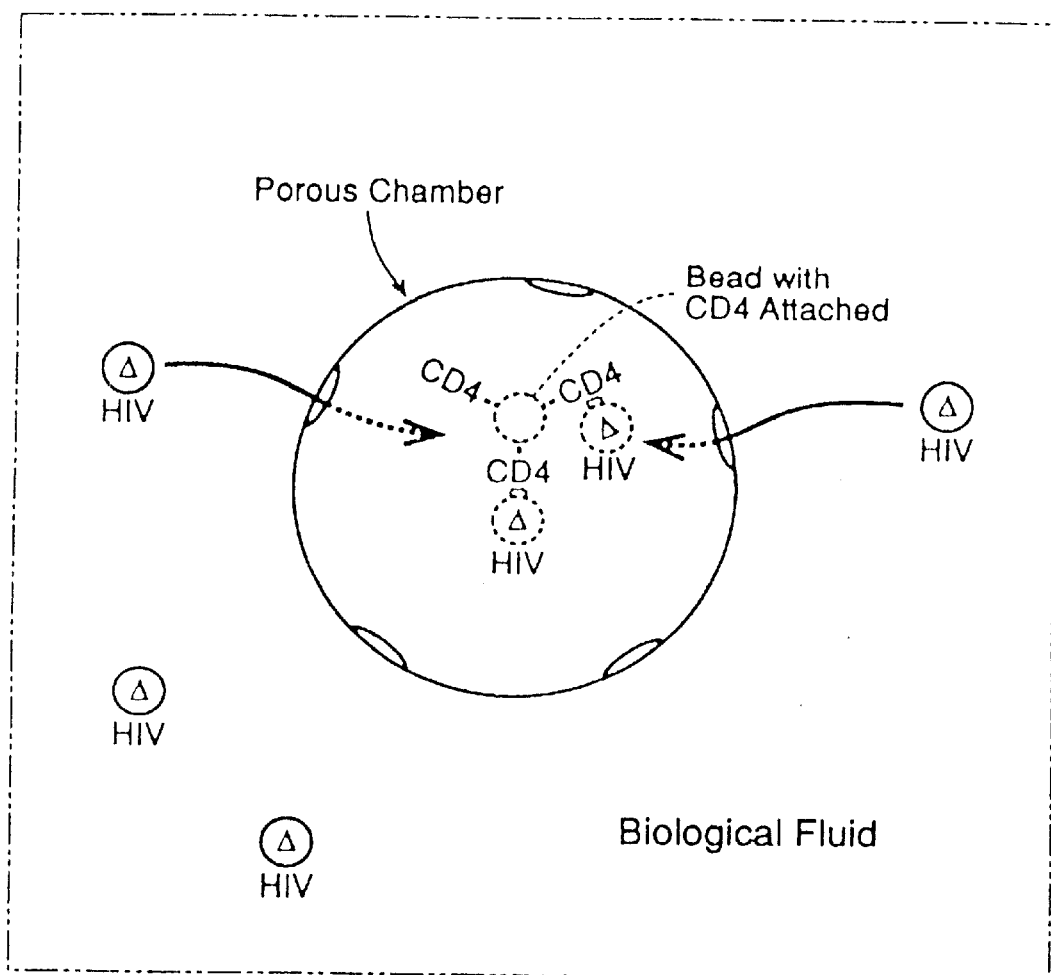

FIG. 8(A). A permeable membrane forming a chamber containing soluble, recombinant CD4 molecules attached to sepharose or similar support beads. The large sphere with holes represents the membrane. The holes of the membrane are large enough to allow HIV virions to enter and small enough to prevent entry of cells containing CD4 receptors. Since the diameter of HIV is ca.100 nm, a hole diameter of between about 50 nm and about 150 nm is sufficient.

Figure 8B:
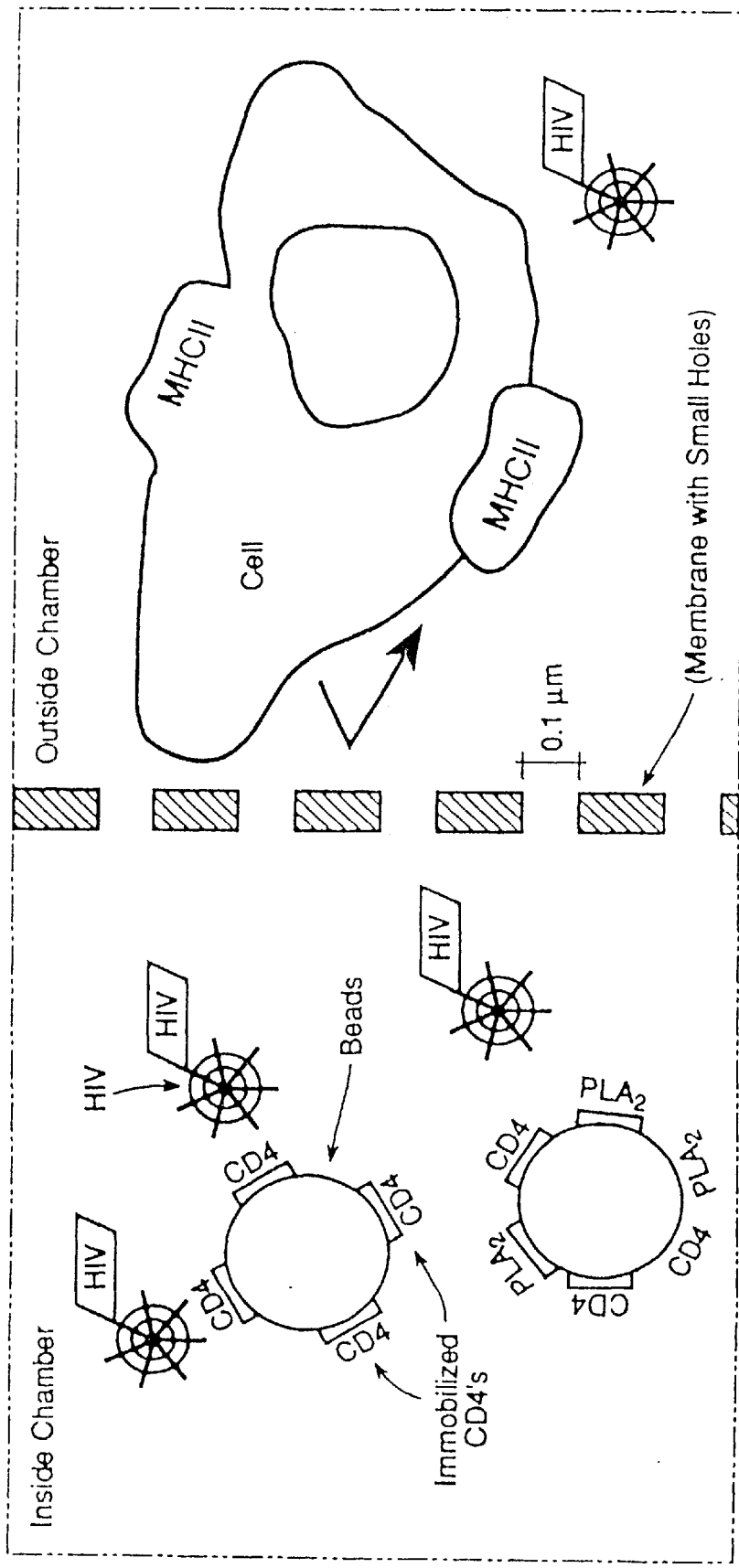

FIG. 8(B). Another version of the membrane showing HIV binding to CD4 immobilized on beads inside the chamber and a cell too large to enter outside the chamber. Also illustrated is both CD4 and $PLA_2$ immobilized on the same bead.

DETAILED DESCRIPTION OF THE INVENTION

The present invention provides a method for treating Hemophilia A or B which comprises implanting in fluid communication with the bloodstream of a mammal in need of such treatment a permeable membrane forming one or more walls of a hollow chamber, a plurality of holes extending through the membrane and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, wherein inactive Factor VII in blood passing through the membrane becomes activated into Factor VIIa upon contact with the activator within the chamber.

The present invention also provides a method for treating Hemophilia A or B which comprises circulating extracorporeally blood from a mammal in need of such treatment through a permeable membrane forming one or more walls of a hollow chamber, a plurality of holes extending through the membrane and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, wherein inactive Factor VII in blood passing through the membrane becomes activated into Factor VIIa upon contact with the activator within the chamber.

The present invention further provides a permeable membrane forming one or more walls of a hollow chamber, and a plurality of holes extending through the membrane and permitting fluid to enter and exit the chamber, each of the holes being sized so that it is large enough to permit inactive Factor VII to enter the chamber and activated Factor VIIa to exit the chamber but small enough to prevent fibrinogen from entering the chamber, a plurality of supports being disposed within the chamber, and an effective amount of a Factor VII activator or a source of the activator being bound to the supports, the Factor VII activator activating inactive Factor VII in blood passing through the membrane into Factor VIIa upon contact with the inactive Factor VII within the chamber.

The present invention is based on the fact that hemophilia patients have normal levels of unactivated Factor VII, and that the patient's own blood therefore contains a potential source of continuous and endogenous Factor VIIa. In order to access the patient's own Factor VII and convert it to VIIa in an on-line manner, without exposing the patient to chronic administration of exogenous proteins, the present invention places an exogenous activator of Factor VII in or near the blood stream, where it can activate Factor VII or VIIa, but in a manner which limits formation of thrombin by the reaction,

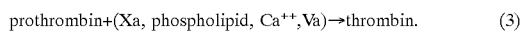

$$\text{prothrombin} + (\text{Xa, phospholipid, Ca}^{++}, \text{Va}) \rightarrow \text{thrombin.} \qquad (3)$$

The term "mammal" as defined herein refers to a human being or an animal.

In one embodiment, the activator of Factor VII is Factor Xa or Factor XIIa. The ability of Factor XIIa to activate Factor VII to VIIa is well known and is described in a popular textbook of hematology (*Hemostasis and Thrombosis,* Robert W. Colman, Jack Hirch, Victor J. Marder, and Edwin W. Salzman, eds, J. B. Lippincott Co., Philadelphia and Toronto, page 9).

In another embodiment, the source of the activator is a cell (examples of suitable cells include procaryotic and eucaryotic cells, preferably mammalian cells, and more preferably human cells). For example, similar to procedure in U.S. Pat. No. 4,670,394, Pollard et al., endothelial cells can be isolated from adrenal medullary tissue, which have characteristic growth patterns, and express different clotting factors (Banerjee, D. K., Omberg, R. I., Youdim, M. B. H., Heldman, E., and Pollard, H. B. (1985) "Endothelial cells from bovine adrenal medulla develop capillary-like growth patterns in vitro" *Prog. Nat. Acad. Sci.* (USA) 82:4702–4706). These cells may be grown on solid matrices, such as cytodex™ beads, and continue to function normally (Forsberg, E. J., Feuerstein, G., Shohami, E., and Pollard, H. B. (1987) "Adenosine triphosphate stimulates inositol phospholipid and prostacyclin formation in adrenal medullary endothelial cells by means of $P_2$—purinergic receptors" *Proc. Nat. Acad. Sci.* (USA) 84:5630–5634). The endothelial cells aggressively grow onto and cover the beads, and the cell-covered beads may be used as a "reagent". For example, cytodex-2™ microcarrier beads (60 mg) may be equilibrated in Dulbocco's phosphate buffered saline and sterilized in an autoclave. The beads may then be added to a 75-cm² flask of confluent endothelial cells, approximately 4–6 days after passage. Endothelial cells grow over and cover the beads within 96 hours. The microcarrier beads and loosely adherent cells may then be dislodged from the flask by tapping the sides of the flask. The beads may be decanted, and allowed to settle. The beads are then washed with 50 ml of serum-free medium, and are immediately available for use as a source of the activator.

The amount of Factor VII activator is an amount effective to treat Hemophilia A or B.

The support is preferably solid and may comprise a wide variety of materials available commercially and widely used for similar purposes in typical protein chemistry applications. For example, a 4% cross-linked beaded agarose which has been chemically activated to contain aldehyde functional groups can be prepared as described in Steers, Cuatrecassas and Pollard, "Isolation of Beta-Galactosidase from *E. coli* K12 by Affinity Chromatography," *J. Biol. Chem.* 246:196–200, 1971; or in Pollard and Steers, "Beta galactosidase from Bacillus megaterium, KM; Isolation by Affinity Chromatography and Characterization of the Active Species, "*Arch. Bioch. Biophys.* 158:650–661, 173. Equivalent activated solid supports can be purchased commercially. For example, PIERCE (Rockford, Ill.) sells a product called "Affilink." PHARMACIA-LKS BIOTECHNOLOGY (Piscataway, N.J.) sells equivalent material called CNBr-activated Sepharose 4B. Other chemistries involving linking amino and carboxy groups through carbodiimide mediated reactions, disulfide-bond formation, and others are available both as a laboratory process and off-the-shelf. The carbodiimide chemistry is also described in detail in Steers, Pollard and Cuatrecassas, 1971 vide supra. Other types of commercially available solid supports included beaded polyacrylamide and porous glass.

The permeable membrane may comprise any container that has the property of being biologically compatible, and having holes in it in the size specified, that is, each of the holes being sized so that it is large enough to permit inactive Factor VII to enter the chamber of the membrane and activated Factor VIIa to exit the chamber of the membrane but small enough to prevent fibrinogen from entering the chamber of the membrane. Examples of membranes include but are not limited to a dialysis bag or a dialysis membrane, a geometric filter, a statistical hole filter, and a cellulose acetate membrane. Preferably, the size of each of the holes in the membrane is less than about 100 angstroms, and most preferably is 40–50 angstroms, which is suitable for a protein of ca. 50,000 daltons. Such diameters can be achieved both with geometric filters (eg., methacrylate filters by PORETICS, INC., Livermore Calif.) or filters with statistical holes (eg. cellulose acetate, from a variety of commercial sources). Such membranes are widely available commercially (e.g., PIERCE, Rockford, Ill.). Dialysis units approved for use in humans suffering kidney disfunction are available in a cassette format with membranes that are suitable in principle. An example is the F60 membrane made of polysulfons by Frosenius Corp., Frankfurt, Germany. The latter device employs convection technology. An example of a cellulose acetate membrane is a Poretics Polycarbonate Track-Etch (PCTE) membrane (Poretics Corporation, Livermore, Calif.).

Membranes have been used previously for endocrine disorders, whereby, human islets have been placed in analogous porous chambers and implanted in diabetic patients. The use of such encapsulated beta cells has been applied most prominently by Dr. P. Lacy of St. Louis, Mo. (e.g., Dionne, K D, Gentile, F. Christenson, L., Aebischer, P., Lysaght, M., Lacy, P E, and Hegre, O D, "Insulin Release Kinetics from Microencapsulated Rat Islets in vitro, "*Diabetes* 40:284A (1991)). On a commercial scale, a "plastic pancreas" has been described in which the encapsulating membrane allows insulin into the blood stream, but prevents the entry of lymphocytes (e.g., BioHydbrid Technologies, Inc. of Shrewsbury, Miss.) as described in *Science:* Sullivan, S J, Maki, T., Borland, K M, Mahoney, M D, Soloman, B A, Muller, T E., Monoco, A P., and Chick, W L. "Biohybrid Artificial Pancreas: Long Term Implantation Studies in Diabetic, Pancreatectomized Dogs," *Science* 252:718–721, 1991) and in *The Washington Post,* May 3, 1991. The islets are thereby protected from anti-islet antibodies, but nonetheless have access to blood glucose concentrations.

Figure 1A:
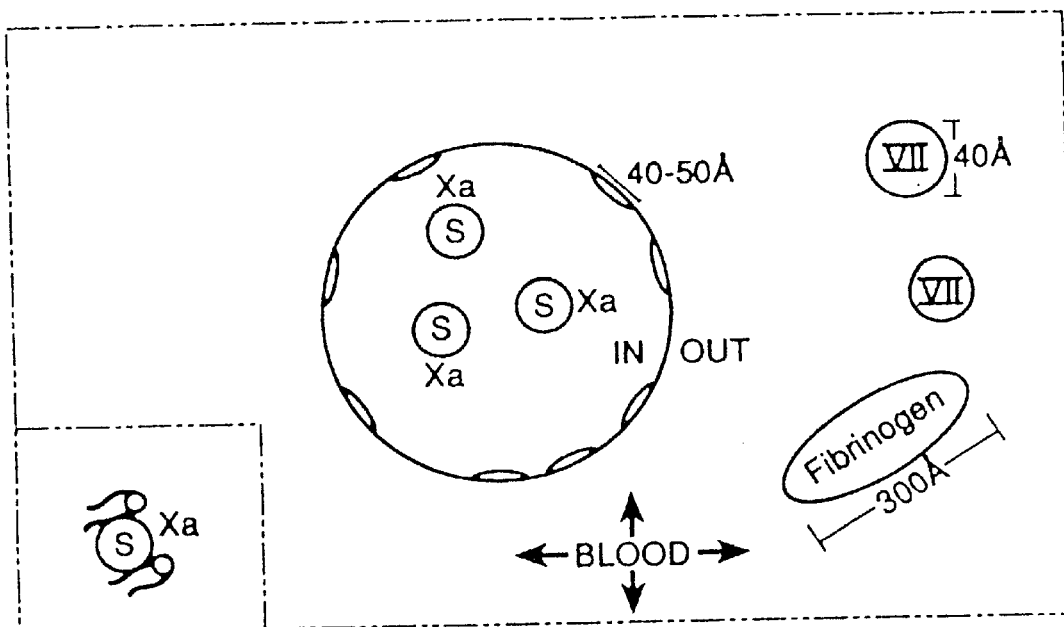
FIG. 1. (A) Permeable membrane containing Factor Xa bound to sepharose or similar support beads. The large sphere with holes represents the permeable membrane. The diameter of the holes is 4–5 nm (40–50 Angstroms). This size is appropriate for Factor VII proteins (see small sphere mixed "VII") contained in BLOOD to enter through the membrane into the chamber. Within the chamber defined by the membrane are sepharose beads (marked "S") bound to Factor Xa molecules. In the BLOOD domain are fibrinogen molecules, ca. 30 nm (300 Angstroms) length, which are too large to enter the membrane into the chamber. INSET: The Xa molecule and phospholipid molecules. The small circles with two strands attached represent phospholipids. The advantage here is that the activity of Factor Xa can be potentiated by phospholipids. (B) Permeable membrane allows inactive Factor VII to enter and activated Factor VIIa to exit. The holes in the walls of the membrane are large enough to admit Factor VII molecules, and to allow the exit of cleaved or activated Factor VIIa molecules. Fibrinogen molecules are too large to enter, so that any danger of coagulation within the chamber is minimized.
Figure 1B:
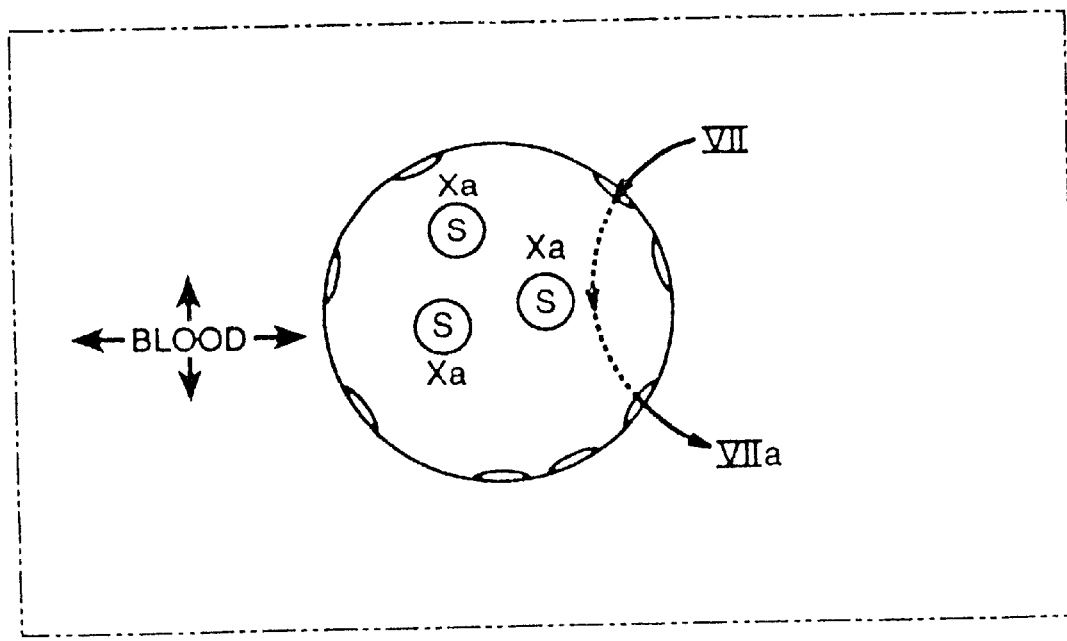

One example of a kidney dialysis cassette is sold by Baxter Travenol and consists of a chamber, through which 250 micron diameter tubes with small holes take blood through and back to the body. Waste products in the blood diffuse into the chamber in exchange for an appropriate ionic mix from the chamber. The operational surface area of the tubes may be as high as 1 square meter. The membrane of the present invention may be represented by the dialysis membrane which makes up the tubes. The interior of the chamber may be the volume enclosing the tubes. This volume may be very small (e.g., 5–10 ml) or even 1000 ml, depending on the need. The application to humans can be done by adapting preexisting kidney dialysis technology. The size of the holes in the Baxter device are reputedly ca. 20 Angstroms. However, the nominal size and the operational size depend on the statistical distribution of holes sizes. By contrast, the hole sizes in the F-60 by Frosenius Corporation may be more appropriate. From this description, the reader will appreciate that the exact geometry of this cassette is the inverse of that shown in FIG. 1A, but the consequences are the same. The pressure of the blood coming into the chamber, either from an arterial source or by pump, is the driving force for the convective membrane function.

In the methods of the present invention, the membrane is implanted so that it is in contact with the patient's blood stream. In this regard, the membrane is filled with solid support complexed or bound to an activator of Factor VII, sterilized and implanted using conventional medical equipment and procedures into the femoral vein, or intraperitoneally. The membrane may be removed by similar surgical procedures. Alternatively, a bypass device may be installed into the patient, and circulation allowed through an arteriovenous bypass (extracorporeal therapy).

The use of the membrane of the present invention avoids generation of substantial amounts of thrombin, (see equation (3)), since there is no Factor V in the chamber within the membrane. Furthermore, interaction between an activator of Factor VII (more specifically, Factor Xa and Factor XIIa) and Factor VII can occur in the absence of phospholipid (Bom, V J J and Bertina, R M (1990) Biochem. J. 265:327–336). Accordingly, in certain circumstances, phospholipid may be unnecessary. Furthermore, even if phospholipid were to be included in the chamber within the membrane, coagulation is avoided by using a membrane with holes too small to permit fibrinogen to enter.

An additional advantage of the present invention is that the activator of Factor VII within the membrane is sequestered from the immune surveillance cells of the host. Thus, an activator of Factor VII from any species may be used. Use of non-human activator would not only reduce cost but would avoid the obligatory problems and infections diseases such as hepatitis and AIDs.

One skilled in the art will appreciate that if the converter of the invention were to stop working, it may be retrieved and replaced.

In addition, the present invention provides a method for preventing AIDS which comprises implanting in a patient with human immunodeficiency virus a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

The present invention also provides a method for preventing AIDS which comprises administering orally to a patient with human immunodeficiency virus a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

The present invention further provides a method for preventing AIDS which comprises circulating extracorporeally blood from a patient with human immunodeficiency virus through a permeable membrane forming one or more walls of a hollow chamber, a plurality of holes extending through the membrane and permitting fluid to enter and exit the chamber, each of the holes being sized so that it is large enough to permit HIV virions to enter the chamber but small enough to prevent cells containing CD4 receptors from entering or exiting the chamber, a plurality of supports being disposed within the chamber, and an effective amount of CD4 molecules being bound to the supports, wherein HIV virions in blood passing through the membrane bind to the CD4 molecules within the chamber and do not exit the chamber.

Lastly, the present invention provides a permeable membrane forming one or more walls of a hollow chamber, and a plurality of holes extending through the membrane and permitting fluid to enter and exit the chamber, each of the holes being sized so that it is large enough to permit virions associated with a virus to enter the chamber but small enough to prevent substances capable of binding to virions from entering or exiting the chamber, a plurality of supports being disposed within the chamber, and an effective amount of a substance being bound to the supports, the substance capable of binding to the virions when placed in contact therewith within the chamber thereby preventing such virions from exiting the chamber.

It is within the confines of the present invention that the foregoing methods and permeable membrane employed therein could be used to trap any virus for which a receptor is known (e.g., the receptor to the human immunodeficiency virus is the CD4 molecule). The methods of the present invention also may be employed where the virus is known to bind to some other agent (e.g., the influenza virus binds to receptors on target cells via hemagglutinin; the hepatitus virus binds to an antibody without mutating away from affinity to the antibody).

The term "substance" as used hereinabove therefore includes soluble receptors, antibodies, or other agents which are capable of binding to a particular virus. The substance is attached or bound to the solid support by methods known to those skilled in the art, examples of which are described below. In the preferred embodiment, the substance is CD4, and most preferably is soluble, recombinant CD4. The virus is preferably HIV.

The solid support referred to hereinabove may comprise a wide variety of materials available commercially and widely used for similar purposes in typical protein chemistry applications. For example, 4% cross-linked beaded agarose which has been chemically activated to contain aldehyde functional groups, may be prepared as described in Steers, Cuatrecassas and Pollard *J. Biol. Chem.* 246:196–200 (1971) or in Pollard and Steers *Arch. Bioch. and Biophys.* 158:650–661 (1973). Equivalent activated solid supports can be purchased commercially. For example, PIERCE (Rockford, Ill.) sells a product called "Affilink." PHARMACIA-LKB BIOTECHNOLOGY (Piscataway, N.J.) sells equivalent material called CNBr-activated Sepharose 4B. Other chemistries involving linking amino and carboxyl groups through carbodiimide mediated reactions, disulfide bond formation and others are available both as a laboratory process and off-the-shelf. The carbodiimide chemistry also is described in detail in Steers, Cuatrecassas and Pollard, 1971 vide supra. Other types of commercially available solid supports fully compatible with the present invention include beaded polyacrylamide and porous glass.

The permeable membrane may comprise any container that has the property of being biologically compatible, and having holes big enough to allow virions associated with the virus to enter, but small enough to prevent entry of substances capable of binding to the virions, such as receptors, antibodies, or other agents. The virions are thus trapped in the chamber. Examples of membranes include but are not limited to a dialysis bag or a dialysis membrane, a geometric filter, a statistical hole filter, and a cellulose acetate membrane. Virions generally range from 15 nm to 300 nm. The preferably range for each hole on the membrane is therefore between about 10 nm and about 400 nm. The size of the holes and the material of the porous chamber will depend on the particular virus to be trapped. Where the virus is HIV, for example, the size between about 50 nm and about 150 nm, and most preferably between about 80 nm and 120 nm is suitable to allow HIV virions (ca.100 nm in diameter) to pass through, yet small enough to prevent entry of CD4. Such diameters can be achieved both with geometric filters (eg., methacrylate filters by PORETICS, INC., Livermore Calif.) or filters with statistical holes (eg. cellulose acetate, from a variety of commercial sources). An example of a cellulose acetate membrane is a Poretics Polycarbonate Track-Etch (PCTE) membrane (Poretics Corporation, Livermore, Calif.).

The permeable membrane may also be a dialysis bag or a dialysis membrane. Dialysis units are approved for use in humans suffering kidney disfunction are available in a cassette format with membranes that are suitable in principle. An example is the F60 membrane of polysulfone by Frosenius Corp., Frankfurt, Germany. This latter device employs convection technology. Such membranes have been used previously for endocrine disorders, whereby human islets have been placed in analogous porous membranes and implanted in diabetic patients. The use of such encapsulated beta cells has been applied most prominently by Dr. P. Lacy of St. Louis, Mo. (e.g., Dionne, et al. *Diabetes* 40:284A (1991). On a commercial scale, a "plastic pancreas" has been described in which the encapsulating membrane allows insulin into the blood stream but prevents entry of lymphocytes (e.g., Biohybrid Technologies, Inc. of Shrewsbury, Mass.), as described in Sullivan, et al. *Science* 252:718–721 (1991) and in *The Washington Post,* May 3, 1991. The islets are thereby protected from anti-islet antibodies, but nonetheless have access to the blood glucose concentrations.

For the methods of present invention, the membrane may be swallowed, or implanted chronically within the peritoneal cavity, off-line or on-line in the blood stream, or in the vaginal, rectal, or urethral orifices of the mammal. For implantation, the membrane is sterilized and implanted using conventional medical equipment and procedures into the femoral vein, or intraperitoneally. The membrane may be removed by similar surgical procedures. Additionally, a bypass device may be installed into the patient, and circulation allowed through an arteriovenous bypass (extrcorporeal therapy). The membrane also may be administered orally in the form of a pill or in the anal or vaginal orifices via a suppository, a diaphragm, or a tampon. The form of the membrane will depend upon the route of administration, as well as the results desired (e.g., treatment or prevention). For example, the use of suppository, diaphragm, or tampon is preferred in methods of prevention. The membrane may be used in conjunction with these devices by methods known to those skilled in the art.

For suppository use, suppository bases which are solid at room temperature and melt or dissolve at body temperature may be employed. Commonly used bases include coca butter, glycerinated gelatin, hydrogenated vegetable oil, polyethylene glycols of various molecular weights, and fatty acid esters of polyethylene stearate.

The membrane also may be encapsulated in an acid-stable, base-labile coating (e.g. an enteric pill which is coated with a substance such as salol which will not dissolve in the stomach or a hexylresorcinol pill which consists of hexylresorcinol covered with a rupture resistant coating that disintegrates in the digestive tract). The pill would be stable in the acid stomach, but would become "activated" as it enters the high pH small intestine. This would be especially of effective in conjunction with AIDS where the membrane would be allowed to traverse the gastrointestinal tract, collecting HIV virions as it goes. With a normal transit time of 6 hours, a continuous presence of the membrane in the G.I.tract could be engineered with q.i.d. dosage.

The amount of CD4 molecules or other substance (i.e. receptor for another virus) bound to the support in an amount effective to treat AIDS (or other known viral-caused disease).

By using the methods of the present invention, the concentration of free virions will decline in the patient over time. The time required to decrease the concentration to acceptable levels will depend upon the placement of the membrane and the concentration of the virus prior to therapy. When the concentration of the virus is sufficient to cause disease in the patient, reducing the concentration of the virus to lower, harmless levels will help treat the disease (e.g. reduce the probability of sustained infection). The membrane may be used prophylactically if the subject is at high risk for the virus (e.g., in the case of HIV, intravenous drug users, homosexuals, or hemophiliacs) but has not been infected with the virus, or if infected, the concentration of the virus is not high enough to initiate the disease. When the substance attached to the solid support is completely bound by virions, the membrane should be removed and replaced. The frequency of replacement will depend on the actual concentration of free virions in the blood.

The efficacy of the above methods may be assessed by following the concentration of the virus in the blood of the subject by using commercially available tests.

It is also within the confines of the present invention that a membrane lytic agent such as a lipolytic enzyme (e.g. phospholipase $A_2$ ($PLA_2$)) or other cytotoxic agents also could be attached by similar technology to the solid support (see FIG. 8(B)). Thus, upon binding of the virus to the substance, the lytic agent would hydrolize the virus lipids, and destroy the virus.

The methods of the present invention offer the following advantages for sequestering HIV. CD4 receptor molecules within the membrane are sequestered from the immune surveillance cells of the patient. If a non-human protein or other factor were to be used in place of the CD4 receptor molecule, no immune reaction would be anticipated. Additionally, the use of the membrane should reduce the likelihood of medical personnel contracting infections from exposure to human blood. The reduction of HIV virion concentration also may lessen the spread of AIDS.

The present invention is described in further detail in the following experimental details section, which sets forth specific examples to aid in understanding the invention and should not be construed to limit in any way the invention as defined in the claims which follow thereafter.

EXPERIMENTAL DETAILS

EXAMPLE 1

Hemophilia A and B

FACTOR Xa. Factor Xa is readily obtainable from bovine or human sources (eg., sigma, St. Louis, Mo.; Kabi-Vitrum, Stockholm Sweden). Factor X can itself be activated to Xa by Russells Viper Venom. Xa is very stable. The presence of Factor Xa may be easily assessed using commercial kits (eg., COATEST, Kabi-Vitrum) which contain the chromogenic substrate S-2222.

ASSAY OF FACTOR VIIa. Factor VIIa can be measured as an extrinsic pathway activity in terms of its ability to combine with Tissue Factor and thereby activate X to Xa. Xa also can be measured by the method described above, or by its ability to clot plasma in the presence of Tissue Factor.

THE PERMEABLE MEMBRANE. The membrane can be prepared from millipore or nucleopore membrane materials, which have defined sized holes. The membranes are available made to order commercially. Cellulose acetate membranes are available from Pierce and Banter-Travenol. A polysulfonate membrane is available from Frosenius.

DIFFUSION OF PURE FACTOR VII ACROSS A CELLULOSE ACETATE MEMBRANE. A Teflon™ structure of 0.5 $cm^2$ was separated from a second compartment, also of Teflon, by a cellulose acetate membrane having a nominal molecular weight cutoff of 50,000 da. A diagram of the structure and the arrangement of solutions is shown in FIG. 2. The solutions on either side were phosphate buffered saline (PBS) and on one side purified human Factor VII had been added. The question was whether Factor VII activity could diffuse across the membrane and elevate the clotting time in the compartment originally lacking the added Factor VII.

As shown in FIG. 3, the clotting time of the PBS solution was ca. 180 seconds, while that of the Factor VII-containing solution was 48 seconds (see column C, control). After incubation for 1 hour at room temperature (23° C.), the clotting time for the PBS side originally lacking Factor VII was reduced to ca. 80 seconds. These data demonstrate that Factor VII can move across a cellulose acetate membrane of defined pore size.

FACTOR Xa CAN RAPIDLY ACTIVATE FACTOR VII TO VIIa. Factor VII may be activated to Factor VIIa by exposure to Factor Xa, calcium and phospholipids. The resulting Factor VIIa causes the clotting time for an assay of tissue factor/VII activation of Factor X to Xa to fall. This is conceptionally called the partial thromboplastin activation time (PTT), and is a stable clinical test. To demonstrate this assay with reagents used in the present invention, the activation of purified human Factor VII to VIIa by Factor Xa, in the presence or absence of calcium was compared.

As shown in FIG. 4, incubation of Factor VII with Factor Xa and phospholipids, without the addition of calcium, only leaves the Factor VII with its original activity. This was observed whether the incubation is for 30 seconds or 20 minutes, and yields identical results of ca. 63 seconds. The crosshatched bars represent this information. However, addition of calcium to the assay activates Factor Xa to cleave Factor VII to Factor VIIa, and the PTT was reduced to 36 seconds. The activity was essentially identical following 20 minutes incubation.

Thus, conversion of Factor VII to Factor VIIa was rapid and the converted product was quite stable (e.g. an early name for Factor VIIa was "stable factor," reflecting this property).

DIFFUSION OF FACTOR VII ACTIVITY FROM FACTOR VIII-DEFICIENT PLASMA TO FACTOR VII-DEFICIENT PLASMA ACROSS A POLYCARBONATE MEMBRANE. The ability of Factor VII in plasma to diffuse across a Poretics™ Polycarbonate Track Etch (PCTE) membrane of defined pore size is shown in FIG. 5. The experiment was performed as follows: A teflon structure with internal volume of 1.0 $cm^3$ was separated from a second test solution by a PCTE membrane. Membranes of pore sizes of 0.01, 0.03 and 0.05 $\mu$m were compared. The two solutions were plasma deficient in Factor VIII, and plasma deficient in Factor VII, respectively. After incubation for 6 hours at 37° C., Factor VII was measured in both chambers using the prothrombin time clotting assay.

As shown in FIG. 5, the initial clotting time of the Factor VII deficient plasma (column C, control) was 120 seconds, while that of the Factor VII in the Factor VIII deficient plasma was 39.3 seconds. Thus, Factor VIII-deficient plasma had essentially control levels of Factor VII, and could serve as a source of Factor VII for replenishment of the deficiency in the Factor VII deficient plasma. Following incubation, as described, the clotting times for the Factor VII deficient plasma declined to near control levels. The different pore sizes were essentially identical, yielding clotting times of 41.2, 37.4, and 43.3 seconds, respectively, for 0.01, 0.03, and 0.05 $\mu$m diameter pore sizes. The Factor VII-dependent clotting times for the Factor VIII deficient plasma rose slightly, consistent with the movement of Factor VII across the membrane into the Factor VII-deficient plasma side.

FIBRINOGEN DOES NOT DIFFUSE ACROSS POLYCARBONATE MEMBRANES WHICH ALLOW DIFFUSION OF FACTOR VII. The ability of Fibrinogen in PBS to diffuse across a Poretics™ polycarbonate Track Etch (PCTE) membrane of defined pore size is shown in FIG. 6. The experiment was performed as follows: A teflon structure with internal volume of 1.0 cm² was separated from a second test solution by a PCTE membrane. Membranes of pore sizes of 0.01, 0.03 and 0.05 μm were compared. The two solutions were PBS alone and PBS containing purified human fibrinogen at a concentration and activity equal to that found an average in human plasma. Fibrinogen was assayed by a conventional method in which activity was estimated from the time thrombin (5 units/ml) could proteolyze the fibrinogen to fibrin and form a clot. For this experiment, 200 μl samples of the 1 ml test solutions were taken for the assays.

As shown in FIG. 6, the clotting time of the PBS solution containing fibrinogen was ca. 38 seconds, while the clotting time for the PBS only solution was ca. 200 seconds. These times were virtually unaffected by incubation for 3 hours at room temperature (23° C.), with pore sizes of 0.01, 0.03 and 0.05 μm. A different experiment, in which incubation was allowed to go for 24 hours, yielded essentially identical results. Thus, the polycarbonate filter with 0.01 μm pore size allows Factor VII to pass through, but retards fibrinogen, thereby preventing the membrane from becoming internally coagulated by concomitant admission of fibrinogen.

COUPLING OF FACTOR Xa TO BEADS IN AN ACTIVE FORM. In order for the invention to work properly, the protein Factor Xa must be able to form a covalent linkage with beads and retain catalytic activity. As shown in FIG. 7, this was accomplished by the following protocol:

Bovine Factor Xa (1.0 mg), obtained from Pierce Biochemicals, was desalted on a PD10 column (Pharmacia), and the active fractions collected in a 500 μl volume. The desalting medium is 0.1 M HEPES/NaOH buffer, pH 7.4 and 0.3 M NaCl. The Factor Xa sample was then immediately mixed with 750 μl of Affigen-10 beads (Pierce, 500 μl settled volume), freshly washed according to the manufacturer's directions. The coupling buffer was identical to the desalting medium, except that the reaction mixture is adjusted to 80 mM $CaCl_2$. Inclusion of the latter salt leads to a ca. 10-fold increase in yield of bound, active Factor Xa. This reaction was allowed to proceed at 4° C. for 12 hours. The beads were then centrifuged at 12,000×g×10 seconds, and then washed three more times in protein-free, calcium-free desalting medium. Finally, the unreacted sites were blocked by resuspending the beads for 24 hours at 4° C. in 1 M glycine, prepared in desalting buffer. The beads were then washed three times in phosphate buffered saline (PBS), and stored in 1.0 ml of this buffer, supplemented with 0.1% NaAzide to prevent bacterial growth.

The activity of the beads was assessed with the clinically utilized COATEST kit (supplied by Helena Labs, Beaumont, Tex., as prepared for distribution by Kabi-Vitrum, Copenhagen). Briefly, kit components consisting of the phospholipids, calcium, and the chromogenic substrate S-2222 were added in the volumes specified by the manufacturer. Different volumes of beads were added and the reaction allowed to proceed for 5 minutes after pre-activation with calcium. The reaction was terminated with 25 μl of 50% acetic acid (HAC), diluted up to a volume of 950 μl, and the absorbance read at 405 nm.

The results of the activity assay are shown in FIG. 7. The vertical axis is the absorbance of the chromic product of S-2222 hydrolysis, and is a specific measure of Factor Xa activity. In FIG. 7(a), the lower horizontal axis is the volume (in μl) of beads added to the COATEST assay. The upper horizontal axis represents the fraction of the total bead preparation added. In FIG. 7(B), the bar graph represents unbound Factor Xa activity found in 40 μl of the supernatant solution from the coupling reaction ("SUP"), and 40 μl aliquots of subsequent washing steps (W1, W2, and W3, respectively). Note that the last washes were essentially without activity, while the adduct-gel matrix possessed substantial activity. The percentage of coupling under these conditions was calculated to be ca. 12%.

EXAMPLE 2

Human Immunodeficiency Virus

Figure 2:
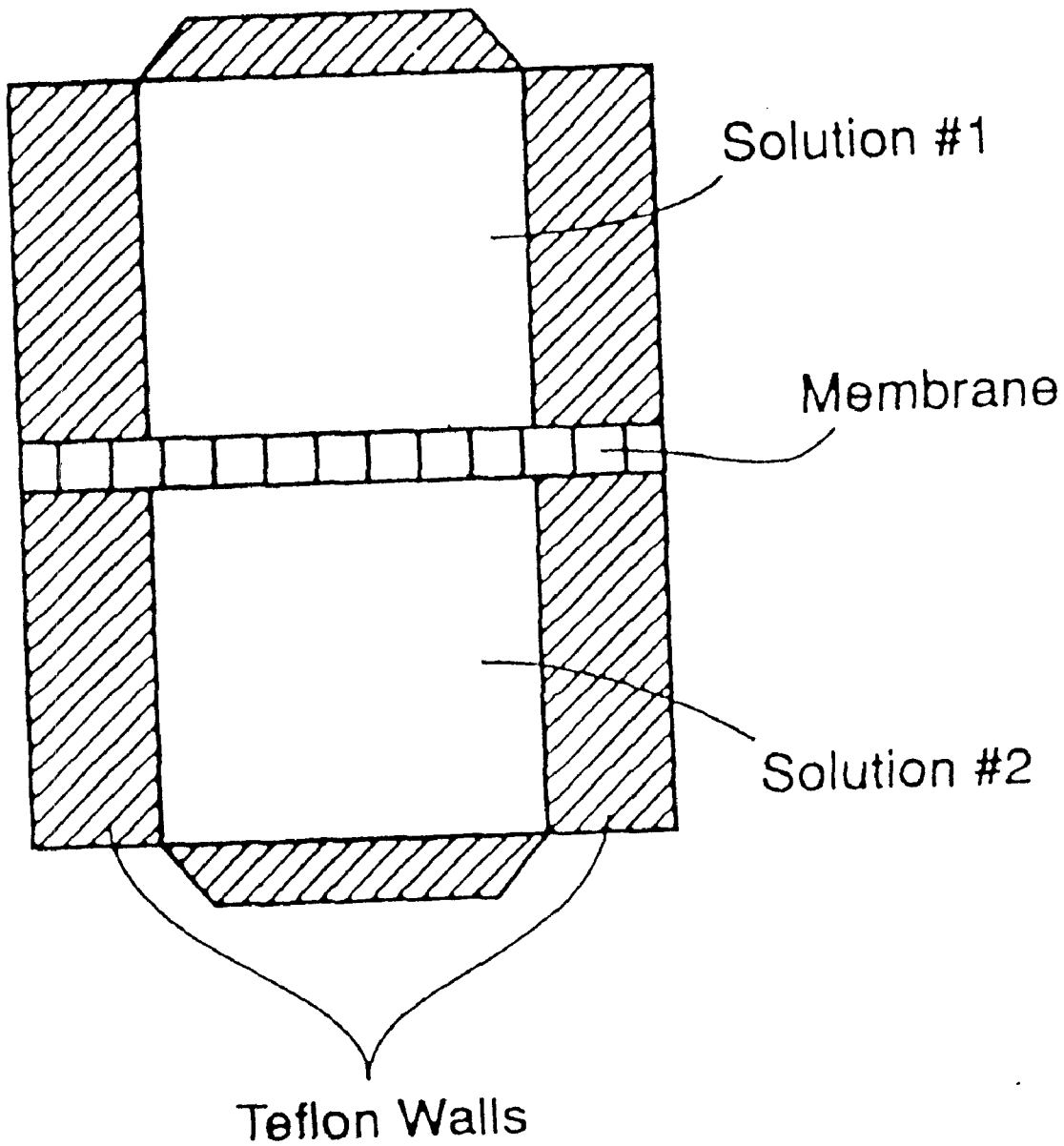
FIG. 2. The membrane as described in Example 1: Teflon structure of 0.5 $cm^3$; composed of two compartments separated by a cellulose acetate membrane having a nominal molecular weight of 50,000 da. The solutions on either side were PBS and purified human Factor VII. The membrane as described in Example 2: Solution #1 contains pure recombinant HIV coat protein fragment, gp120, at a concentration of ca. 20 $\mu$g/ml in a total volume of 0.5 ml phosphate buffered saline (PBS). Solution #2 contains pure recombinant soluble CD4, covalently attached to Affigel-10 beads (Pierce, Rockford, Ill.). The gp120 and the CD4 were obtained from American Bio-Technology, Inc., Cambridge, Mass. The substituted beams are in a final concentration of 50% (vol./vol.) and are in a total volume of 0.5 ml PBS. As a control, beads also were prepared substituted with the primary amine Tris(hydroxymethyl)amino methane (TRS, Calbiochem). In this embodiment, the membrane is a Poretics polycarbonate Trach-Etch (PCTE) membrane (Poretics Corporation, Livermore, Calif.) with a 0.05 $\mu$m pore size. It is exceptionally pure, and has negligible adsorption or absorption properties. Similarly, the Teflon structure is made of low reactivity material.
Figure 3:
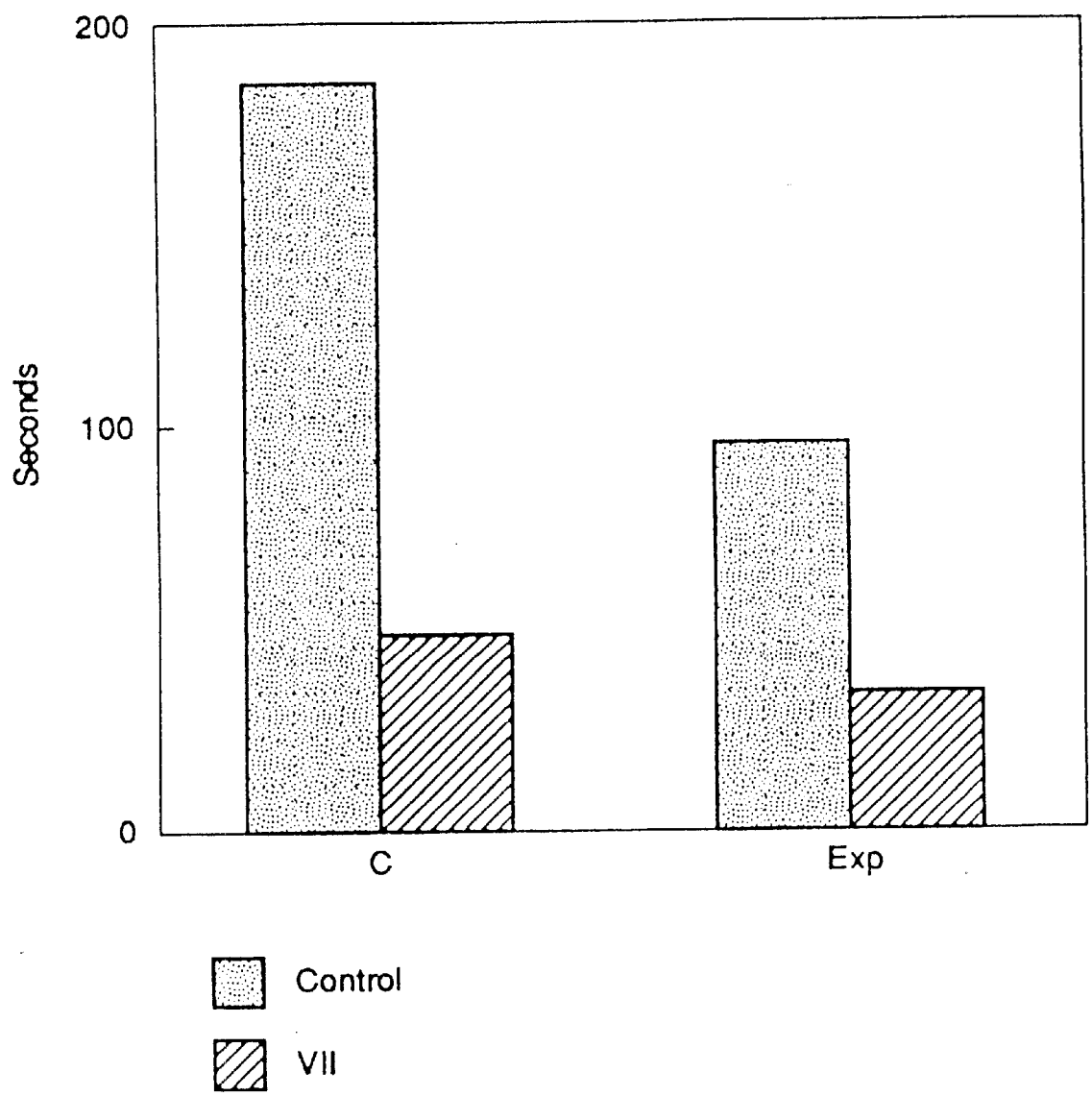
FIG. 3. Diffusion of Factor VII (pure) across 50 kd cellulose acetate membrane.

BINDING OF GP120 TO CD4 BEADS. Solution #1 (see FIG. 2) contained pure recombinant HIV coat protein fragment, gp120, at a concentration of ca. 20 μg/ml in a total volume of 0.5 ml phosphate buffered saline (PBS). Solution #2 contained pure recombinant soluble CD4, covalently attached to Affigel-10 beads (Pierce, Rockford, Ill.) as described in Example 1. The gp120 and the CD4 were obtained from American Bio-Technology, Inc., Cambridge, Mass. The substituted beads were in a final concentration of 50% (vol./vol.) and in a total volume of 0.5 ml PBS. As a control, beads were also prepared which were substituted with the primary amine Tris(hydroxymethyl)amino methane (TRS, Calbiochem). The membrane used was a Poretics Polycarbonate Track-Etch (PCTE) membrane (Poretics Corporation, Livermore, Calif.) with a 0.05 μm pore size. This membrane is exceptionally pure, and has negligible adsorption or adsorbtion properties. Similarly, the Teflon structure is itself made of low reactivity material.

The experiment was initiated by introducing the gp120 in solution #1 to a system to which either the CD4 beads, or the control TRIS beads, in solution #2 had already been added. The system was allowed to oscillate on a rotary table at 4° C. for 8 hours. Samples were then removed from each side and analyzed by both SDS gel, to verify that no degradation had occurred, and by protein determination to verify directly whether changes in distribution of gp120 had occurred. The gels used were 8% NOVEX gels. Protein was determined by micro-Bradford using bovine serum albumin as the standard.

As shown in the following table, the compartment containing CD4 beads was able to accumulate 73.7% of the available gp120, while the control compartment containing TRIS beads was only able to accumulate 25.4%. Reference here is to accumulation rather than binding because, in theory, some of the gp120 diffusing into the bead-laden chamber equilibrates freely in the internal solution, rather than being bound to the beads. Since each compartment is identical in volume, one should anticipate that if gp120 could diffuse easily through the membrane, and not be appreciably bound within the chamber, the initial concentration of gp120 should be reduced by 50%. In fact, as shown in the table, the initial gp120 mass of 9.46 μg in solution #1 was reduced by 55.6% to 4.2 μg. However, in the case of the CD4 bead chamber, there was no detectable free gp120 in solution #2 at the end of the incubation period. Thus, any gp120 that entered the chamber immediately bound to the CD4 beads. By contrast, approximately 3 μg of gp120 was found free in the chamber containing TRIS-beads. Presumably, the remainder of the gp120 binds to the control TRIS beads.

| gp-120 μg | CD4 beads | Tris beads |
|---|---|---|
| total | 9.46 | 9.46 |
| Solution #1, final | 2.49 | 4.20 |
| Solution #2, final (free) | zero | 2.86 |
| % bound to beads | 73.7 | 25.4 |

Other uses of the invention could include the following:

Detoxification:

One general use of this invention would be to detoxify a person or other mammal. One example of this use would be to attach a target substance, to which the toxin binds, to the solid supports within the chamber. The chamber is placed into the mammal in contact with the blood. The toxin in the could then diffuse into the chamber and be immobilized or inactivated. An example of an application might be against a toxin such as sarin. Sarin forms a covalent complex with the enzyme acetylcholine esterase at the neuromuscular junction. In this application acetylcholine esterase would be attached to the solid support. Sarin circulating in the blood would diffuse into the chamber, and bind to the acetylcholine esterase. Once the bond is formed, sarin is no longer toxic to the system, and is thus inactivated. Other examples of detoxification involve binding of mercury or lead by specific immobilized chelators.

Other types of detoxification implants could be employed to treat heroin, cocaine, alcohol, or nicotine addictions.

The holes of the membrane would be sized only large enough to allow only the small toxin molecules to enter the chamber.

Use as an anti-microbial agent:

An anti-microbial use of this invention would be to provide a treatment modality for a person or other mammal that has bacteria circulating in the bloodstream that needs to be reduced. One manifestation could protect a mammal from various causes of septic shock. An example of such bacteria might be anthrax. In this situation, antibodies against anthrax bacteria could be immobilized on the supports within the chamber. The chamber is placed into the system, in contact with the blood. Bacteria in the blood would diffuse into the chamber and be bound to the antibody. This method could similarly be used of treatments of Pseudomonas species, staphylococcus species, and streptococcus species.

The holes of the membrane would be sized large enough to allow the microbe to enter the chamber.

Anti-inflammatory implant system:

Another use of this implant can be used to reduce the inflammatory process in a person or other mammal. In this example, antibodies to proinflammatory cytokines such as IL8, IL1 or TNF-alpha could be immobilized within the chamber. The changer is placed into the system, in contact with the blood. Circulating cytokines that enter the chamber might be thereby bound and inactivated. This would reduce the presence of the proinflammatory cytokine circulating within the system. For example, one could immobilize a monoclonal anti-TNFalpha antibody such as C2a and thereby suppress rheumatoid arthritis symptoms with the implant. In a second example, one could immobilize myelin basic protein, or fragments or analogues of this protein on the supports of the chamber. The chamber is placed into the system, in contact with the blood. The myelin protein would attract the autoantibodies causing multiple sclerosis. In a third example, one could immobilize poliovirus antibody onto the supports of the chamber. The chamber is placed into the system, in contact with the blood. The immobilized polio virus antibody would trap fragments of poliovirus thought to be circulating in the CSF of persons afflicted with post-polio syndrome. The implants could also be distributed throughout the system, perhaps in the central nervous system as well as in the peritoneal cavity, to heighten the effect.

The holes of the membrane would be sized large enough to allow the specific products to enter the chamber.

Drug delivery system:

A general use of this invention as a drug delivery system would be to use the implant as a means of encapsulating cells that naturally secrete, or that have been engineered to secrete, therapeutic substances, and implanting the encapsulated cells into a person or other mammal. For example, proteins have been identified which have anti-cancer properties. Some cells found in nature secrete these substances; other cells could be genetically engineered to secrete these substances. Examples of such therapeutic substances could include, but not be limited to, tumor suppressor gene products, such as annexin 7; tumor suppressor gene peptides such as in the example of p19; and angiostatin proteins, which block tumor dependent capillary growth. The cell would be immobilized on a support within the membrane chamber. The chamber is placed into the system, in contact with the blood. The cells secrete the therapeutic substance into the blood that distributes the therapeutic agent.

The holes of the membrane would be sized small enough to protect the cells on the supports from immunologic attack, but would be large enough to permit the lower molecular weight proteins or peptides to escape into the circulation.

Treatment of a non-infectious disease:

An implant can be used to treat a noninfectious disease. This method cant be applied to the treatment of diabetes. The method involves attaching 2 types of diabetes-specific antigens to the supports within the chamber. Both Type I and Type II diabetes are characterized by high levels of anti-insulin antibodies (I-AA) and anti-glutamic acid decarboxylase antibodies (AGDA). Suppression of these antibodies is associated with increased survival of islets in patients. Therefore, the antigens, insulin and glutamic acid decarboxylase, would be attached to supports within the chamber. The chamber would then be placed within the mammal, in contact with the circulating blood. The antibodies in the blood would bind to the antigens within the chamber, resulting in a decrease of the circulating anti-insulin and anti-glutamic acid decarboxylase antibodies. The level of insulin within mammal itself would not be affected, as the added insulin would only be within the chamber. This would result in increased survival of islets in the patients.

Holes of the chamber would be sized sufficiently large to permit antibodies to enter the chamber.

Chamber modification:

In addition to the forms of chamber previously described, the chamber could have a region that would allow it to be affixed to the inside of the abdominal wall. The region would also have a diaphragm that would allow penetration of a syringe. The syringe could be used to remove or add materials. The materials might include, but not be limited to, replacements of used up support and bound materials. In this manner, other supports and bound materials could be substituted with the use of the syringe in the event the previous material is no longer required, and a different material is required. Thus, new materials could even be introduced into the chamber in the case of a new illness once the implant is in place.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A biocompatible permeable membrane forming one or more walls of a hollow chamber suitable for extracorporeal use or implantation in a human body; a plurality of holes extending through the membrane and permitting fluid to enter and exit the chamber, each of the holes being sized so that it is large enough to permit a virus to enter the chamber but small enough to prevent substances capable of binding to the virus from entering or exiting the chamber when placed in contact with bodily fluids; a plurality of supports disposed within the chamber; and an effective amount of a substance bound to the supports, the substance capable of binding to the virus when placed in contact therewith within the chamber, thereby preventing such virus from exiting the chamber.

2. The membrane of claim 1, wherein the permeable membrane is selected from the group consisting of a dialysis membrane, a geometric filter, a statistical hole filter, and a cellulose acetate membrane.

3. The membrane of claim 1, wherein each of the holes is sized from about 10 nm to about 400 nm in diameter.

4. The membrane of claim 1, wherein the supports are selected from the group consisting of sepharose, polyacrylamide and glass beads.

5. The membrane of claim 1, wherein the virus is a human immunodeficiency virus.

6. The membrane of claim 1, wherein the substance is a CD4 molecule.

7. The membrane of claim 6, wherein the CD4 molecule is recombinantly made.

8. The membrane of claim 1, wherein the permeable membrane is selected from the group consisting of a geometric filter and a statistical hole filter.

9. The membrane of claim 8, wherein the statistical hole filter is made of cellulose acetate.

10. The membrane of claim 8, wherein the geometric filter is selected from the group consisting of methacrylate and polycarbonate.

* * * * *